(12) United States Patent
Qian et al.

(10) Patent No.: US 11,138,806 B1
(45) Date of Patent: Oct. 5, 2021

(54) DISTRIBUTED AUGMENTED REALITY IMAGE DISPLAY AND GENERATION OF COMPOSITE IMAGES

(71) Applicant: MediVis, Inc., New York, NY (US)

(72) Inventors: Long Qian, Brooklyn, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 17/121,283

(22) Filed: Dec. 14, 2020

(51) Int. Cl.
| | |
|---|---|
| *G06T 19/00* | (2011.01) |
| *G16H 30/40* | (2018.01) |
| *G16H 50/50* | (2018.01) |
| *G16H 30/20* | (2018.01) |
| *G06F 21/62* | (2013.01) |

(52) U.S. Cl.
CPC ........... *G06T 19/006* (2013.01); *G16H 30/20* (2018.01); *G16H 30/40* (2018.01); *G16H 50/50* (2018.01); *G06F 21/6245* (2013.01); *G06T 2210/41* (2013.01); *G06T 2219/024* (2013.01)

(58) Field of Classification Search
CPC ........... G06T 2210/41; G06T 2219/024; G06T 19/006; G16H 30/20; G16H 30/40; G16H 50/50; G06F 21/6245
See application file for complete search history.

(56) References Cited

U.S. PATENT DOCUMENTS

| | | | | |
|---|---|---|---|---|
| 2013/0135312 | A1* | 5/2013 | Yang | G06T 15/20 345/427 |
| 2015/0262412 | A1* | 9/2015 | Gruber | G06T 19/006 345/426 |
| 2017/0367771 | A1* | 12/2017 | Tako | G06T 19/003 |
| 2019/0139300 | A1* | 5/2019 | Kirchberg | G01B 11/026 |

* cited by examiner

*Primary Examiner* — Sing-Wai Wu
(74) *Attorney, Agent, or Firm* — Cognition IP, P.C.; Edward Steakley; Rajesh Fotedar

(57) ABSTRACT

Various embodiments of an apparatus, methods, systems and computer program products described herein are directed to a workstation computing system(s) ("workstation") that receives camera pose data from a camera(s) disposed on a first headset device. The workstation receives camera image data comprising one or more images portraying a current view of the camera. The workstation generates a rendering of the 3D model of medical data for display within a composite image. The workstation generates one or more portions of the composite image based on the camera image data. The workstation generates and displays a composite image to include simultaneous and contiguous portrayal of the rendering of the 3D model of medical data with the one or more portions based on the camera image data.

20 Claims, 15 Drawing Sheets

DISTRIBUTED AUGMENTED REALITY IMAGE DISPLAY AND GENERATION OF COMPOSITE IMAGES

BACKGROUND

Current conventional systems have limitations with regard to two-dimensional (2D) and three-dimensional (3D) images in surgical settings. Surgical planning is necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Various embodiments of an apparatus, methods, systems and computer program products described herein are directed to a composite image generation and distribution of Augmented Reality (AR) images to headset devices. According to various embodiments, a workstation computing system(s) ("workstation") may be in continuous communication with a plurality of headset devices concurrently worn be different users. The workstation receives camera pose data from a camera(s) disposed on a first headset device. The workstation receives camera image data comprising one or more images portraying a current view of the camera. The workstation generates a rendering of the 3D model of medical data for display within a composite image. The workstation generates one or more portions of the composite image based on the camera image data. The workstation generates and displays a composite image to include simultaneous and contiguous portrayal of the rendering of the 3D model of medical data with the one or more portions based on the camera image data.

The embodiments described herein generate and display a composite image during a camera mode (i.e. a composite image mode). The embodiments described herein may further operates in a distribution mode in which a distinct base image is generated for and sent to each headset device. During camera mode, a workstation(s) may display a composite image with respect to a particular headset device and may still concurrently generate and send base images to other headset device.

Various embodiments include a module(s) and/or one or more functionalities to redact privacy information/data (such as medical data), to encrypt information/data and to anonymize data to ensure the confidentiality and security of user, patient and system information/data as well as compliance with medical regulatory and privacy law(s) in the United State and/or international jurisdictions.

According to various embodiments, a camera functionality sends image data based on a view of a camera on a particular mixed reality smartglass headset device ("smartglass device"). The image data is received by the workstation and incorporated into a rendered composite image in which one or more portions of the received image data are displayed concurrently with a rendering of the 3D model. For example, the workstation may render a composited display of the 3D model such that the composited display includes a rendered view of the 3D model concurrently presented with a rendered background based on the received image data.

With display of the composite image at the workstation based on a particular user's smartglass device, a user situated at the workstation may view a rendering of the 3D model that has a physical orientation in the unified coordinate system in alignment with the physical orientation of a view of a rendering of the 3D model displayed by the particular user's smartglass device. In addition, by incorporating background segments from the image data received from particular user's smartglass device around the view of the rendering of the 3D model at the workstation, the user at the workstation is able to visually perceive the peripheral background that the particular user is experiencing while the particular user concurrently views the smartglass device display.

According to various embodiments, various embodiments are further directed towards distributing multiple different AR base images to a plurality of headset devices. The workstation receives first device data from a first headset device and generates for the first headset device a first base image of the 3D model of medical data. The first base image is determined according to a transformation of a first portion of the 3D model of medical data according to the first device data of the first headset device. Stated differently, the base image is determined according to the relative transformation between the 3D model and first headset device. The workstation receives second device data from a second headset device and generates for the second headset device a second base image of the 3D model of medical data. The second base image is determined according to a transformation of a second portion of the 3D model of medical data according to the second device data of the second headset device. The workstation sends the first base image to the first headset device for an AR display resulting from post-processing predictions by the first headset device. The workstation further sends the second base image to the second headset device for an AR display resulting from post-processing prediction by the second headset device. It is understood that in some embodiments a base image may be a stereo image. In such embodiments that generate a stereo base image, the stereo base image is determined according to the transformation as described herein but also according data received from the headset device that represents the user's interpupillary distance data.

According to various embodiments, there may be two users and each concurrently wears their own smartglass devices. The workstation generates, via a rendering algorithm(s), two different base images where a respective base image corresponds to a particular user. The workstation generates a two-dimensional (2D) image, such as a 2D AR based image (AR base image), based on device pose data received from a corresponding smartglass device. Device pose data represents an instance(s) of a physical orientation of a smartglass device in the 3D space defined by the unified coordinate system.

The workstation applies at least a portion of the device pose data to the 3D model in order to generate the AR base image such that the AR base image is a view of a portion of the 3D model from the perspective of a user wearing the corresponding smartglass device that provided the device pose data. For example, a different AR base image may be generated and distributed for post-processing by each smartglass device amongst a plurality of smartglass devices during a medical procedure or during a planning session of a medical procedure. Each smartglass device may display an AR image based on the same 3D model of medical data whereby each displayed AR image is a modification of a received AR base image such that the displayed AR image updates the received AR base image according to a predicted physical orientation and position of a corresponding user's smartglass device.

According to various embodiments, a headset device may generate and send user manipulation data that represents a change(s) of a position(s) of one or more sensors worn by a user wearing the respective headset device. It is understood the sensors are associated with the respective headset device. The sensor position change(s) represents a position change of user-selected portion of an AR image currently displayed by the respective headset device as a result of post-processing. The sensor position change further represents a direction, rotation and acceleration of a sensor(s) in the 3D space as defined by the unified coordinate system.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

Figure 1A:
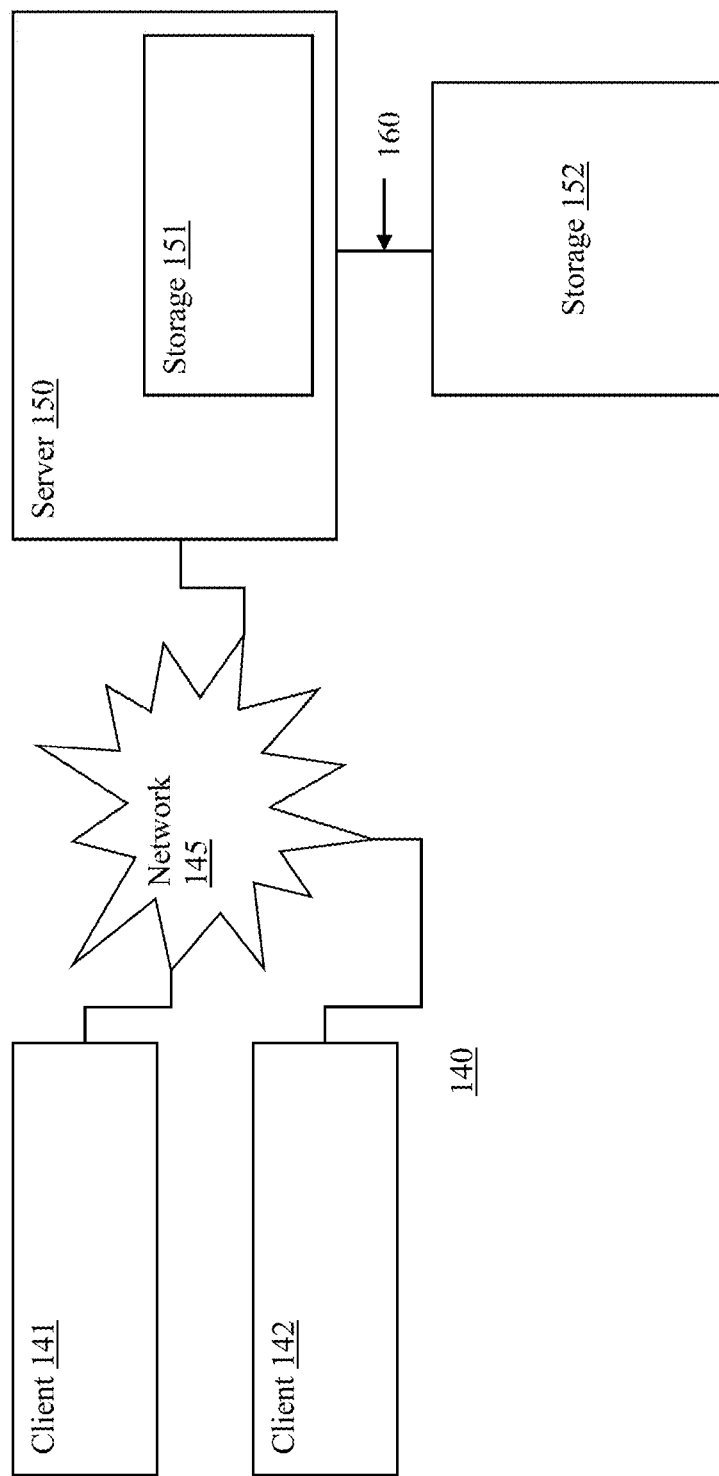
FIG. 1A is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

A diagram of exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, local area network (LAN), wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
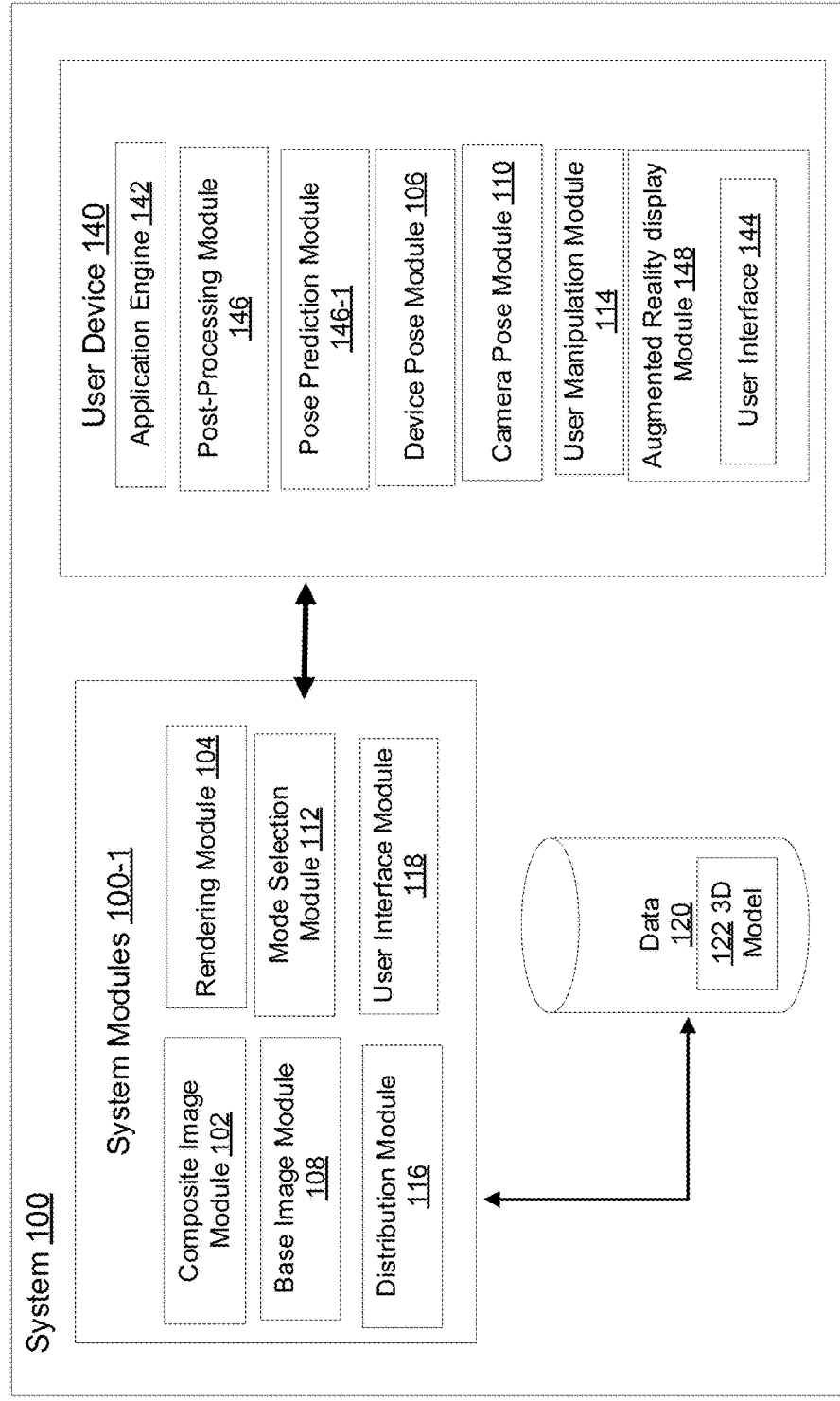
FIG. 1B is a diagram illustrating an exemplary environment in which some embodiments may operate.

FIG. 1B illustrates a block diagram of an example system 100 for various embodiments that includes system modules 100-1, such as: a composite image module 102, a rendering module 104, a device pose module 106, a base image module 108, a camera pose module 110, a mode selection module 112, a user manipulation module 114, a distribution module 116 and a user interface (U.I.) module 118.

The system 100 also includes one or more user devices 140 (such as one or more headset devices) to display output, via a user interface 144 generated by an application engine 142. The user device includes a post-processing module 146 and an Augmented Reality display module 148 for generation and display of an Augmented Reality image and/or an Augmented Reality user interface 144. The post-processing module includes a pose prediction module 146-1. It is understood that the user device(s) 140 may further include one or more of the modules 102, 104, 106, 108, 110, 112, 114, 116, 118 or respective portions of the modules 102 . . . 118 may be distributed and implemented amongst a plurality of user devices 140 and one or more workstations.

The composite image module 102 of the system 100 may perform functionality as illustrated in FIGS. 2A, 3A, 4A, 4B, 4C, 6A and 6B.

The rendering module 104 of the system 100 may perform functionality as illustrated in FIGS. 2A, 2B, 3A, 3B, 4A, 4B, 4C, 5A, 5B, 5C 6A and 6B ("2A-6B").

The device pose module 106 of the system 100 may perform functionality illustrated in FIGS. 2A-6B.

The base image module 108 of the system 100 may perform functionality illustrated in FIGS. 2A-6B.

The camera pose module 110 of the system 100 may perform functionality as illustrated in FIGS. 2A-6B.

The mode selection module 112 of the system 100 may perform functionality as illustrated in FIGS. 2A, 2B, 3A and 3B.

The user manipulation module 114 of the system 100 may perform functionality as illustrated in FIGS. 2A, 2B, 3A, 3B, 6A and 6B.

The distribution module 116 of the system 100 may perform functionality as illustrated in FIGS. 2B, 3A, 3B, 4A, 4B, 4C, 5A, 5B, 5C and 6B.

The user interface module 118 of the system 100 may display information based on functionality as illustrated in FIGS. 2A-6B.

The post-processing module 146 and pose prediction module 146-1 of the system 100 may perform functionality as illustrated in FIGS. 2B, 3A, 3B, 4A, 4B, 4C, 5A, 5B and 5C.

The Augmented Reality (AR) Display module 148 of the system 100 may display on a user interface 144 information based on functionality as illustrated in FIGS. 2A-6B.

Any module or component of the system 100 may have access to a 3D model of medical data 122 or may have one or more portions of the 3D model 122 stored locally. While the databases(s) 120 is displayed separately, the databases and information maintained in a database may be combined together or further separated in a manner the promotes retrieval and storage efficiency and/or data security.

Figure 2A:
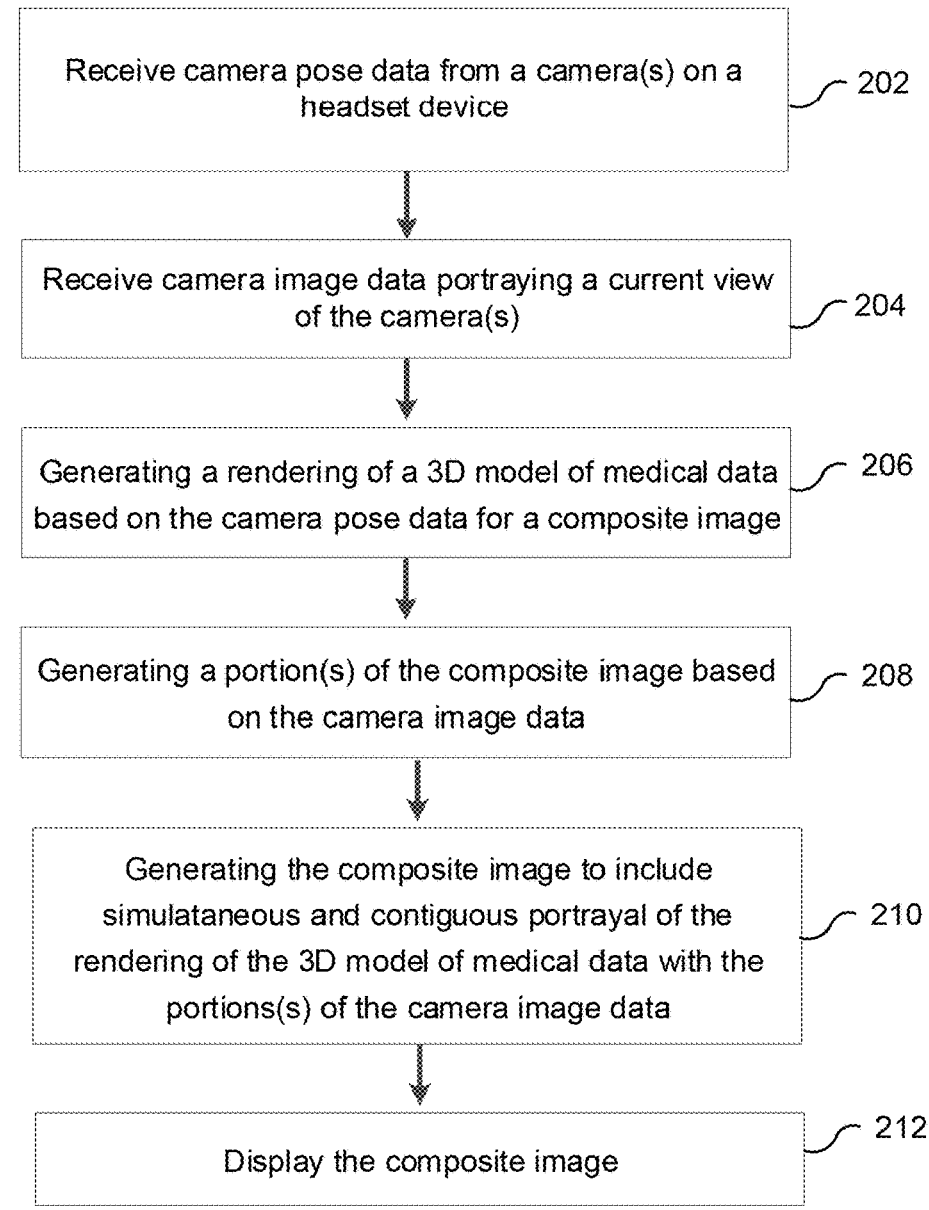
FIG. 2A is a diagram illustrating an exemplary method that may be performed in some embodiments.

As shown in flowchart 200 of FIG. 2A, a workstation receives camera pose data from camera(s) disposed on a first headset device (Act 202). In various embodiments, the camera pose data represents a physical orientation and position of a camera in a three-dimensional (3D) space as defined by a unified coordinate system for the rendering of a 3D model of medical data. The workstation stores and/or has access to a storage location of the medical data. The medical data may be, for example, CT scan data and/or MIl data. The medical data can be any type of medical data and is not limited to CT scan data and/or MRI data. The workstation further stores and/or has access to a storage location of the 3D-model based on the medical data. It is understood that various embodiments are not limited to implementing a workstation and may utilize and implement any type of computing system(s).

It is understood that the first headset device may be included amongst a plurality of headset devices and each headset device is currently worn by a respective different user. Each headset device continually monitors, captures and updates its data, such as camera data and device data. Each respective portion of any type of data captured by a headset device may includes a timestamp indicating a moment in time at which the data was captured.

The workstation receives camera image data comprising one or more images portraying a current view of the camera (Act 204) The camera pose data may be received by the workstation during a camera mode (also known as a composite image mode). The workstation generates a rendering of the 3D model of medical data for display within a composite image (Act 206). The rendering of the 3D model of medical data includes presentation of one or more portions of the 3D model of medical data having respective coordinate positions in the unified coordinate system that align with the camera pose data. The workstation may utilize one or more rendering algorithms to generate a rendering of the 3D model to present a perspective view of a portion(s) of the 3D model according to the camera pose data.

The workstation generates one or more portions of the composite image based on the camera image data (Act 208). The workstation generates the composite image to include simultaneous and contiguous portrayal of the rendering of the 3D model of medical data with the one or more portions based on the camera image data (Act 210). The workstation displays the composite image at the workstation (Act 212).

In various embodiments, a camera functionality of a particular smartglass device sends image data based on a view of a camera(s) on that particular smartglass device. The image data is received by the workstation and incorporated into a composite image in which one or more portions of the received image data are displayed concurrently with the rendering of the 3D model. For example, the workstation may render a composited display of the 3D model such that composited display includes the rendered view of the 3D-model surrounded by a rendered background based on the received image data. A user(s) at the workstation may thereby be presented with a view of the display presented to the user wearing the particular smartglass device along with the peripheral and background visual context that the user is also perceiving while that user focuses attention on the smartglass display.

Figure 2B:
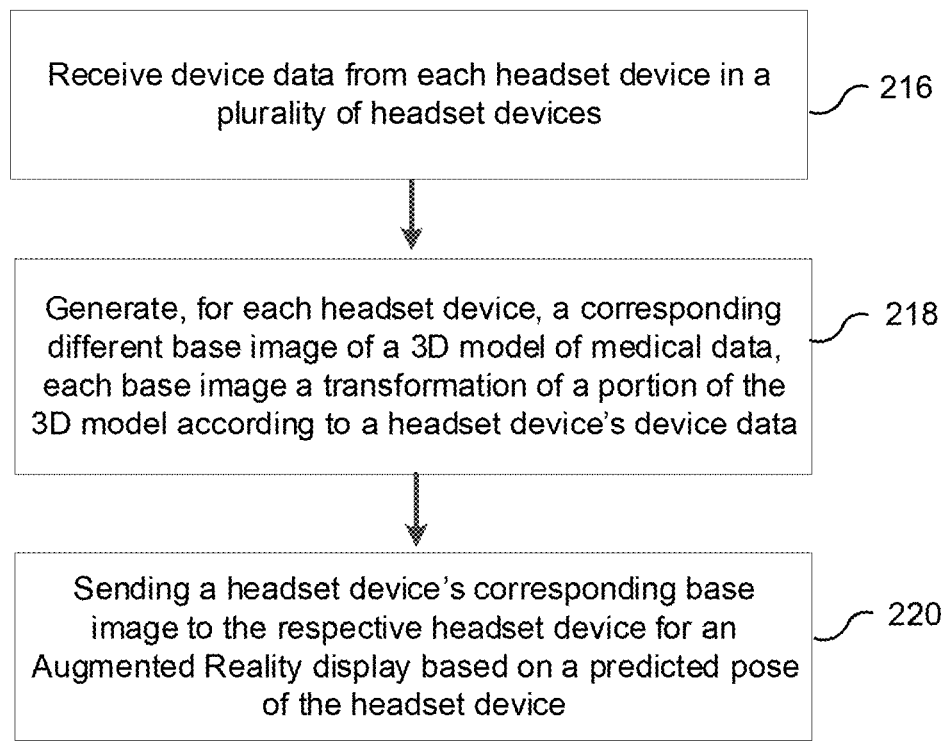
FIG. 2B is a diagram illustrating an exemplary method that may be performed in some embodiments.

As shown in flowchart 214 of FIG. 2B, when the camera mode (or composite image mode) is terminated, the workstation switches to support distribution of AR image to a plurality of headset devices. The workstation receives first device data from a first headset device and second device data from a second headset device (Act 216). In various embodiments, the workstation continually receives various instances of device data captured by each headset device in the plurality of headset devices. The workstation processes the continually received device data for concurrent and continual generation and distribution of a plurality of different AR images, where each different AR image generated by the workstation is distributed for display only at a particular headset device.

In various embodiments, various portions of the device pose data represent successive representations of the physical orientation and position of a respective headset device according to the unified coordinate system. For example, the device pose data represents a current position and a current rotation of the respective headset device in the 3D space as defined by the unified coordinate system at a first moment in time. Subsequent device pose data may represent a different physical orientation and position of the respective headset device resulting from head movement (or any type of body movement) of the user.

In addition, device data received by the workstation may further include various instances of user manipulation data. In various embodiments, user manipulation data represents a change(s) at least in part of a position of a sensor(s) worn by a user wearing the respective headset device. For example, a smartglass device monitors and captures the user manipulation data based on the orientation, direction and velocity of one or more hand movements of a user wearing the smartglass device and also wearing hand sensors capable of detecting the user's hand movements. The smartglass device sends the user manipulation data to the workstation.

The change of the position of a sensor(s) represents a change of a position of a user-selected portion of an AR image currently displayed as a result of post-processing by the respective headset device worn by the user. In various embodiments, the position change represents changes in the direction, rotation and/or acceleration of a sensor(s)s in the 3D space as defined by the unified coordinate system. For example, a smartglass device monitors and captures the user manipulation data based on the orientation, direction and velocity of one or more hand movements of a user wearing the smartglass and wearing one or more hand sensors to detect one or more hand movements.

The workstation generates, for the first headset device a first base image of the 3D model of medical data and a second base image of the 3D model for the second headset device (Act 218). In various embodiments, the first base image is defined as a result of a transformation of a first portion of the 3D model of medical data according to the first device data of the first headset device. The second base image is defined as a result of a transformation of a second portion of the 3D model of medical data according to the second device data of the second headset device.

For example, the workstation emulates a virtual camera for each user wearing a smartglass device and implements the virtual camera to generate a base image of the 3D-model for each user based on the respective user's pose or manipulation data. The workstation generates a user's base image of the 3D model by applying that user's pose or user manipulation data to the unified coordinated system of the 3D model. The workstation identifies a portion(s) of the 3D model at a plurality of coordinates of the unified coordinated system to be portrayed in a visual plane defined by the user's pose or user manipulation data.

The workstation sends the first base image to the first headset device for an Augmented Reality (AR) display based on a first predicted pose of the first headset device and sends the second base image to the second headset device for an AR display based on a second predicted pose of second headset device (Act 220).

According to various embodiments, the smartglass device receives a base image rendered by the workstation according to device poses previously sent by the smartglass device. The received base image has a timestamp that represents the point in time of the device pose(s) upon which it is based. However, there may be latency between when the workstation generated the base image for the smartglass device and when the smartglass device receives and presents the base images. Further, the pose of the smartglass device may have been modified and merely displaying the received base image while the smartglass is oriented according to its most current pose results in a display of a base image that conflicts with the user's actual and true perspective as represented by the most current pose of the smartglass device. To account for this conflict between the base image and the user's actual and true perspective resulting from latency, the smartglass performs post-processing on the received base image prior before displaying the base image.

For example, the smartglass device receives a base image(s) from the workstation. As the smartglass receives various base images generated by the workstation, the smartglass device continually captures current device pose data and generates predicted pose data based at least in part on its current pose data and/or historical pose data. The predicted pose data represents a most up-to-date predicted physical orientation of the smartglass device when the smartglass device presents the AR image. As such the predicted pose data thereby represents a change or modification of a position and/or a rotation in previous device pose data used by the workstation to generate a base image received by the smartglass device. It is understood that base images from the workstation and current device post data captured at the smartglass device each have a corresponding timestamp.

The smartglass device updates the base image generated by the workstation based on applying post-processing to the base image according to the predicted pose data. It is understood that the post-processing occurs prior to generation of any display by the first headset device based in part on the first base image.

The post-processing by the smartglass device accounts for a latency between the timestamp of the received base image(s) by modifying the first base image based at least in part on according to predicted device pose data. For example, to generate the predicted pose data, the smartglass receives a base image generated by the workstation according to smartglass pose data (p1) with timestamp (t1). When the smartglass device receives the base image, the smartglass predicts the physical orientation and position of the smartglass at the moment the base image is to be displayed to the user. By predicting the smartglass' orientation and position, the post-processing can adjust the base image to ensure that the base image is displayed at a perspective view that is in alignment with the user's visual field at that moment—instead of at the previous timestamp (t1).

According to various embodiments, AR image display by the smartglass device may occur according to a predetermined schedule, to allow for identification a point in time at which the smartglass device is to display an AR image. By identifying the precise point in time for AR image display, the smartglass may predict it's likely pose data that will be different than the pose data for the previous timestamp (t1) and modification of the base image will be based on the difference between the earlier pose data (for t1) and the predicted pose data. The smartglass device may implement a variety of algorithms to generate predicted pose data such as, but not limited to, Kalman filter, linear extrapolation and/or any type (or combination of) machine learning techniques.

Figure 3A:
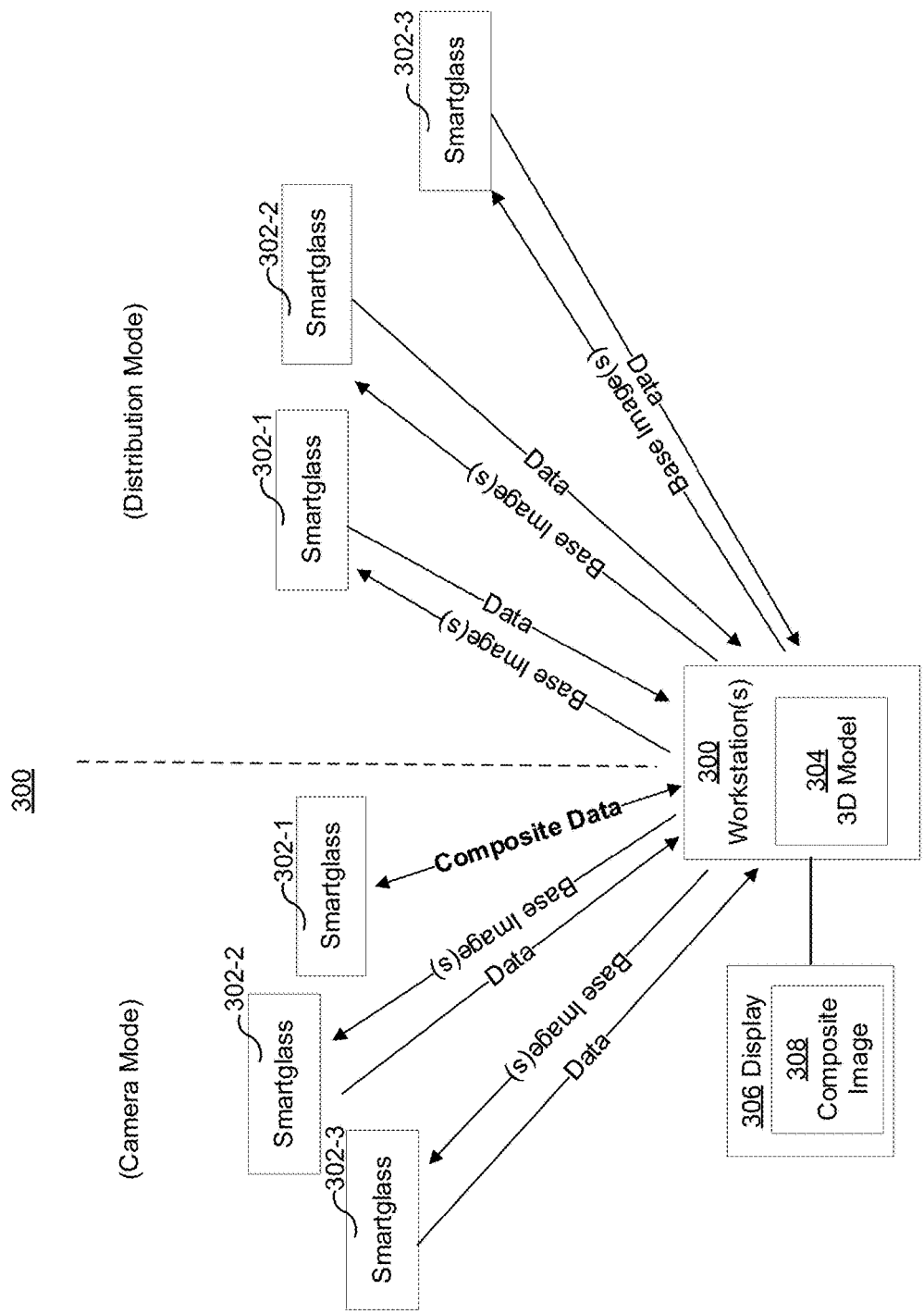
FIGS. 3A and 3B are each a diagram illustrating an exemplary environment in which some embodiments may operate.

As shown in diagram 300 of FIG. 3A, during a camera mode (i.e., composite image mode), a workstation 300 receives data from a particular smartglass device 302-1. The particular smartglass device 302-1 is included in a plurality of smartglass devices 302-1, 302-2, 302-3. The workstation 300 accesses a 3D model of medical data and generates a composite image 308 based on a rendering of the 3D model and a portion(s) of the data received from the particular smartglass device 302-1. It is understood that the data received from the particular smartglass device 302-1 is any data described herein as being utilized with respect to composite image generation during the camera mode (i.e., composite image mode). For example, the composite data may include at least in part one or more portions of camera data. The workstation 300 triggers display of the composite image 308 at a workstation display 306.

During a distribution mode, the workstation 300 continually receives data from each device in the plurality of smartglass devices 302-1, 302-2, 302-3. For each smartglass device 302-1, 302-2, 302-3, the workstation 300 generates base image based on a rendering of the 3D model 304 according to a respective smartglass device's data. The workstation sends to each smartglass device 302-1, 302-2, 302-3 a corresponding base image.

Figure 3B:
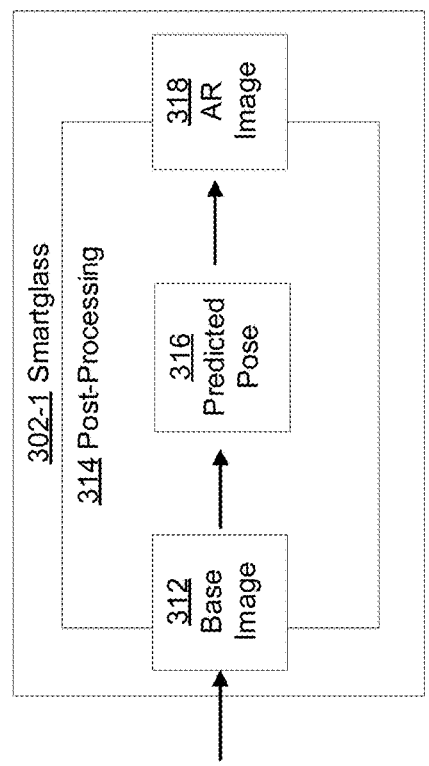

As shown in diagram 310 of FIG. 3B, during the distribution mode, a smartglass device 302-1 receives a base image 312 and determines a visualization of the 3D model 304 according to predicted pose data 316. The smartglass device 302-1 modifies the base image 312 according to the predicted pose data 316 in order to account for latency between a timestamp of the pose data used for generation of the base image and a predicted physical orientation and position of the smartglass device 302-1 at an interval of a fixed AR image display schedule.

Figure 4A:
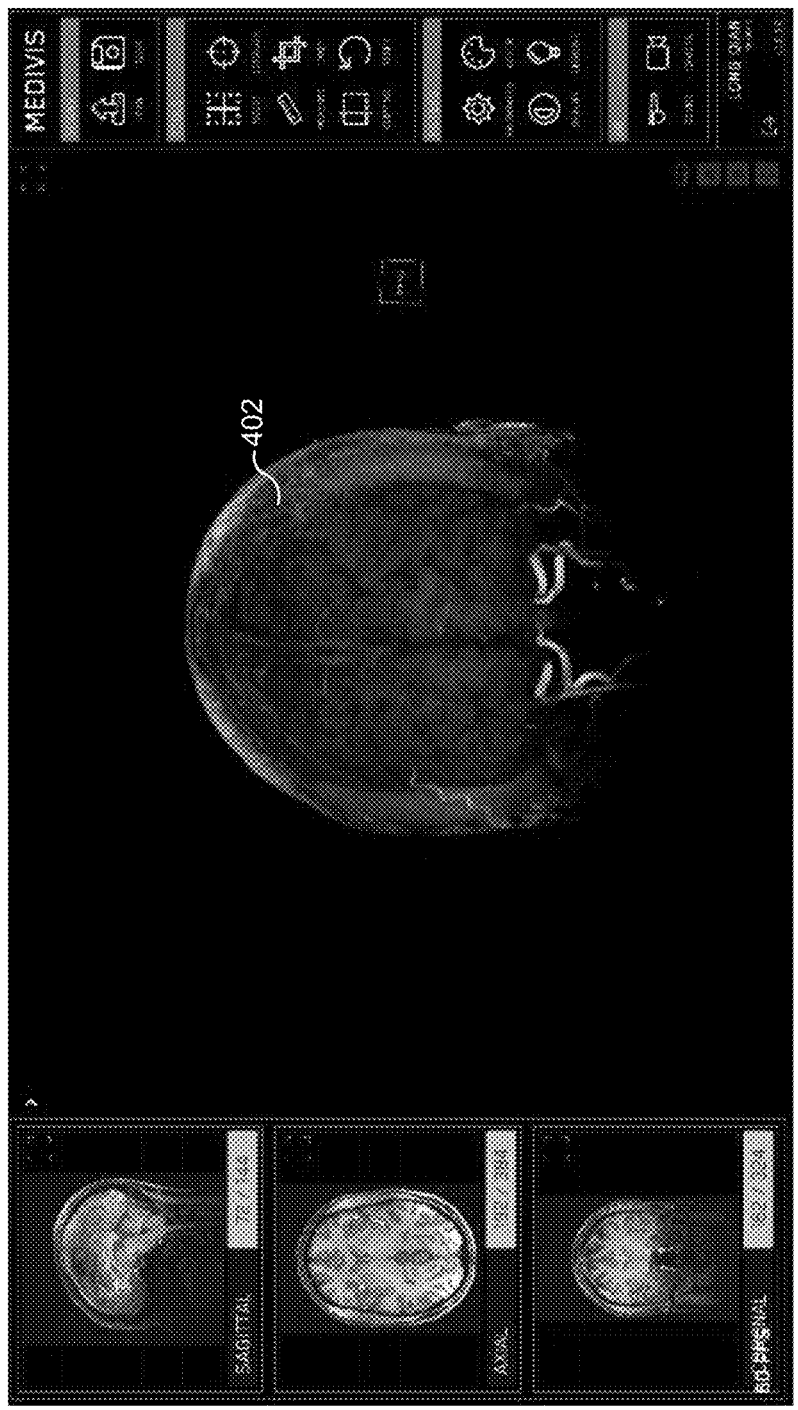
FIGS. 4A, 4B and 4C are each a diagram illustrating an exemplary environment in which some embodiments may operate.

As shown in FIG. 4A, diagram 400 provides an illustration of a rendering of a first perspective view 402 of a portion(s) of a 3D model of medical data.

Figure 4B:
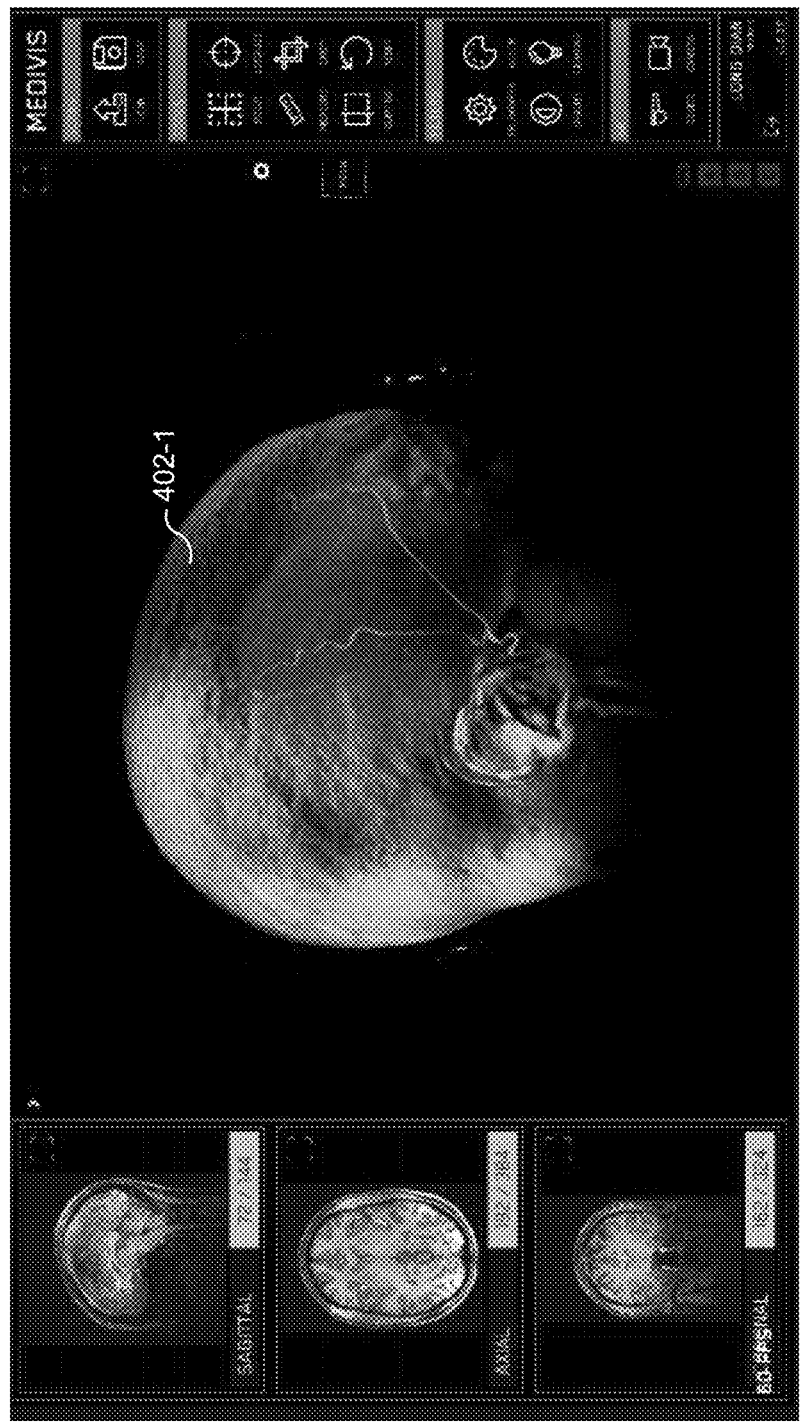
Figure 4C:
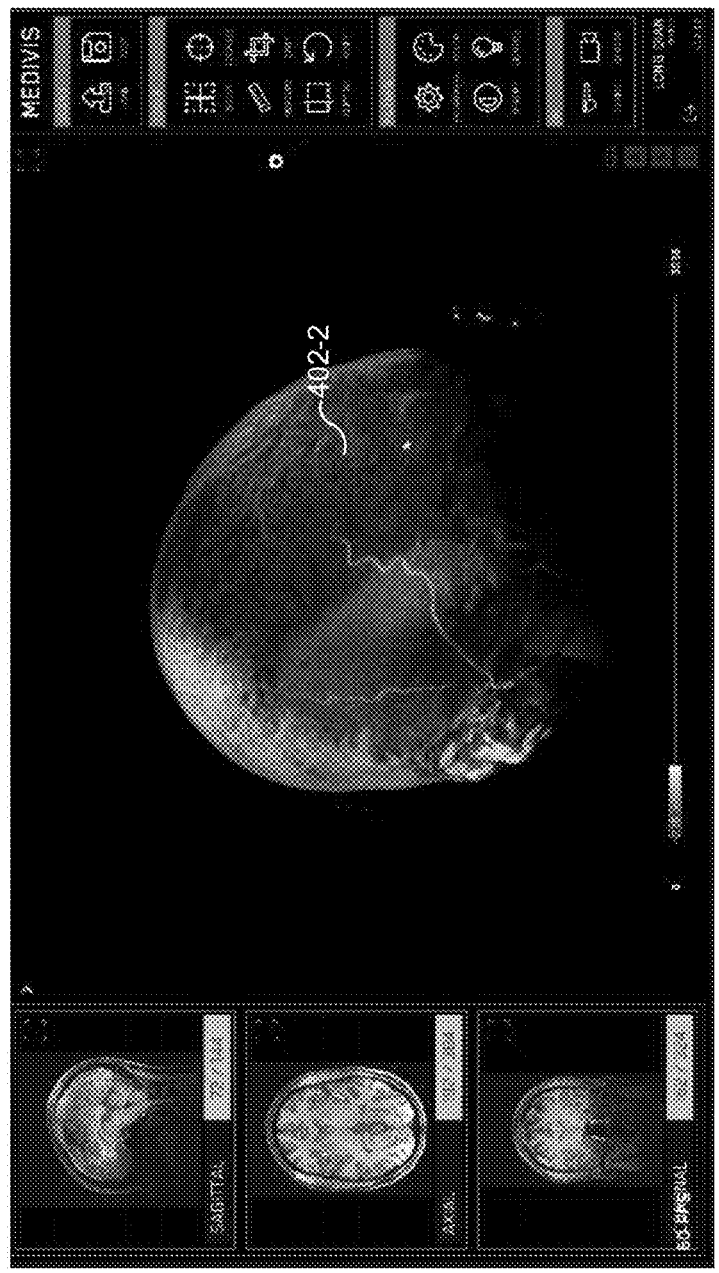

As shown in FIG. 4B, diagram 404 provides an illustration of a rendering of a second perspective view 402-1 of a portion(s) of the 3D model of medical data As shown in FIG. 4C, diagram 406 provides an illustration of a rendering of a third perspective view 402-2 of a portion(s) of a 3D model of medical data.

Figure 5A:
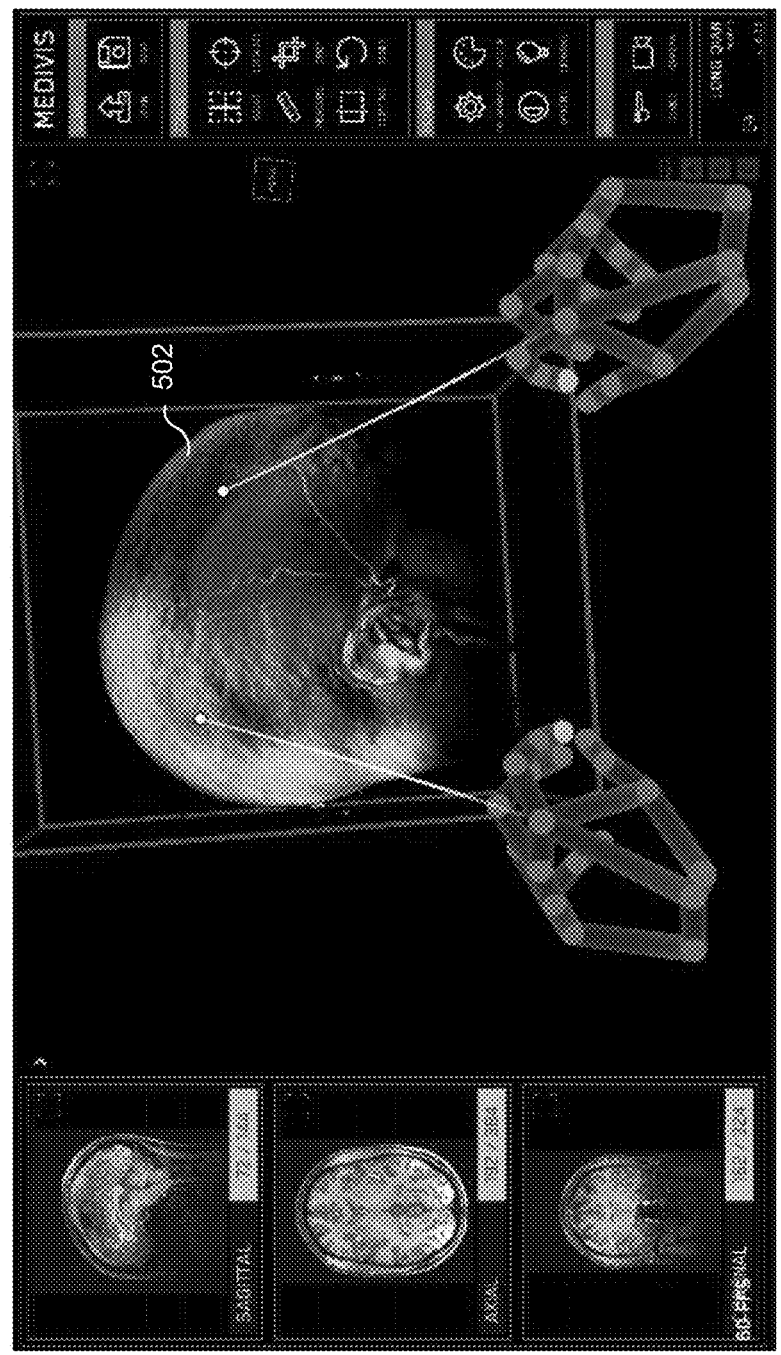
FIGS. 5A, 5B and 5C are each a diagram illustrating an exemplary environment in which some embodiments may operate.

As shown in FIG. 5A, diagram 500 provides an illustration of an AR image 502 generated by a smartglass device for presentation to a user wearing the smartglass device during the distribution mode (and/or camera mode). The AR image 502 is generated by post-processing of a base image with latency adjustment according to predicted pose data generated by the post-processing at the smartglass device.

Figure 5B:
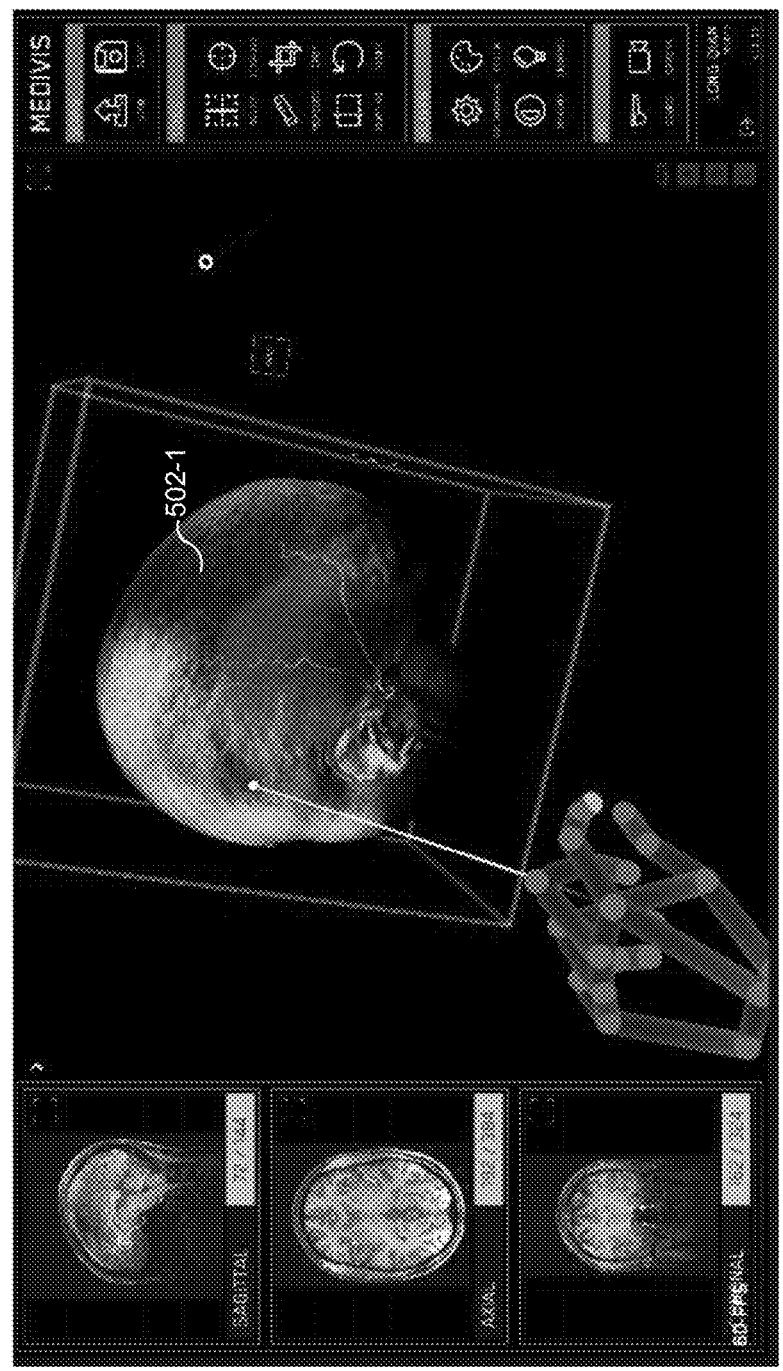

As shown in FIG. 5B, diagram 504 provides an illustration of an AR image 502-1 generated by the smartglass device. The device pose data for the base image of the AR image 502-1 represents a change in physical orientation of the smartglass device due to movement of the user (or movement of the user's head). Display of the AR image 502-1 provides a presentation of the rendered 3-D model as stationary, but the new AR image 502-1 is generated to display the stationary 3-D model towards the left of the user's visual field as the device pose data and the predicted device pose data represent and infer, respectively, that the user is moving (will move) towards the right.

Figure 5C:
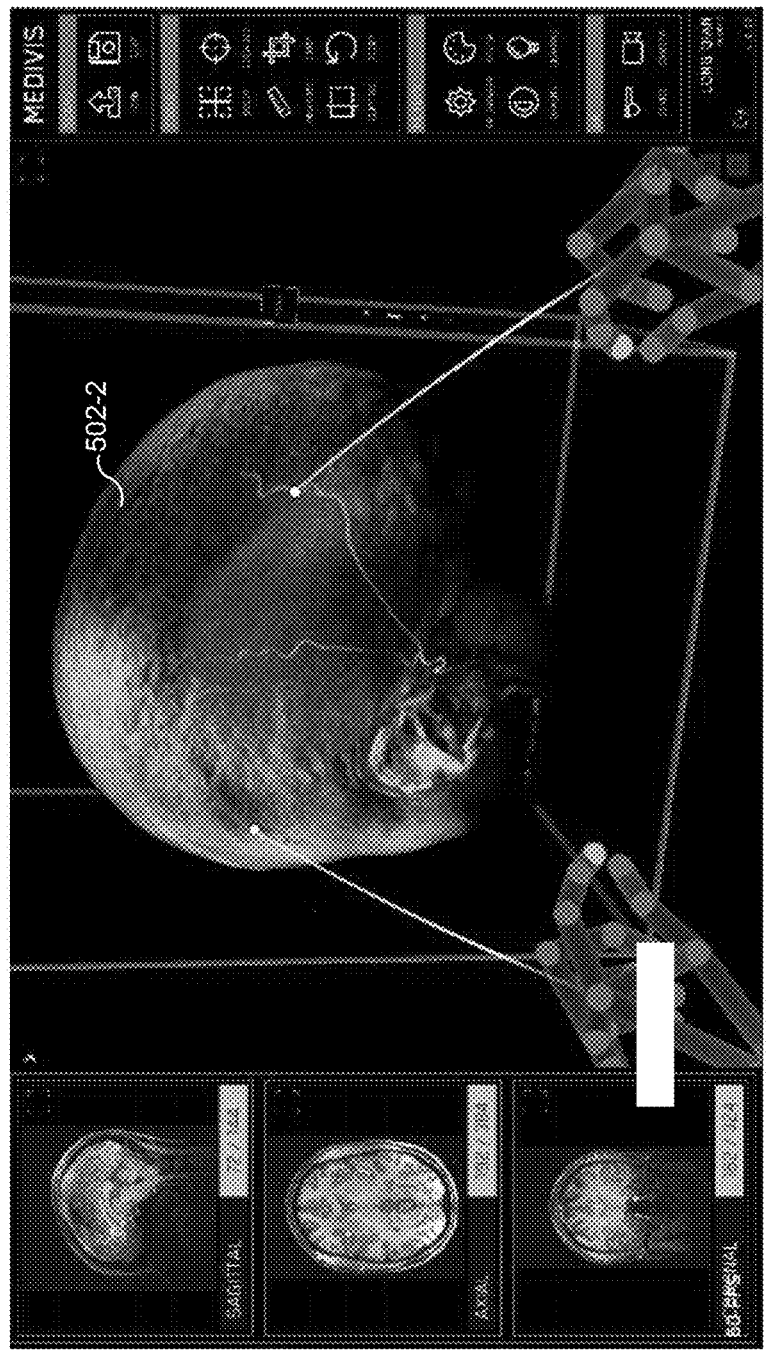

As shown in FIG. 5C, diagram 506 provides an illustration of an AR image 502-2 generated by the smartglass device. The device pose data for the base image of the AR image 502-2 represents a subsequent change in physical orientation of the smartglass device due to additional movement of the user (or movement of the user's head) forward and towards the left. Display of the AR image 502-2 still provides a presentation of the rendered 3-D model as stationary, but the new AR image 502-2 is generated to display the stationary 3-D model closer to the center of the user's visual field than the previous AR image 502-1—since the device pose data and the predicted device pose data represent that the user is moving (will move) forward and towards the left.

Figure 6A:
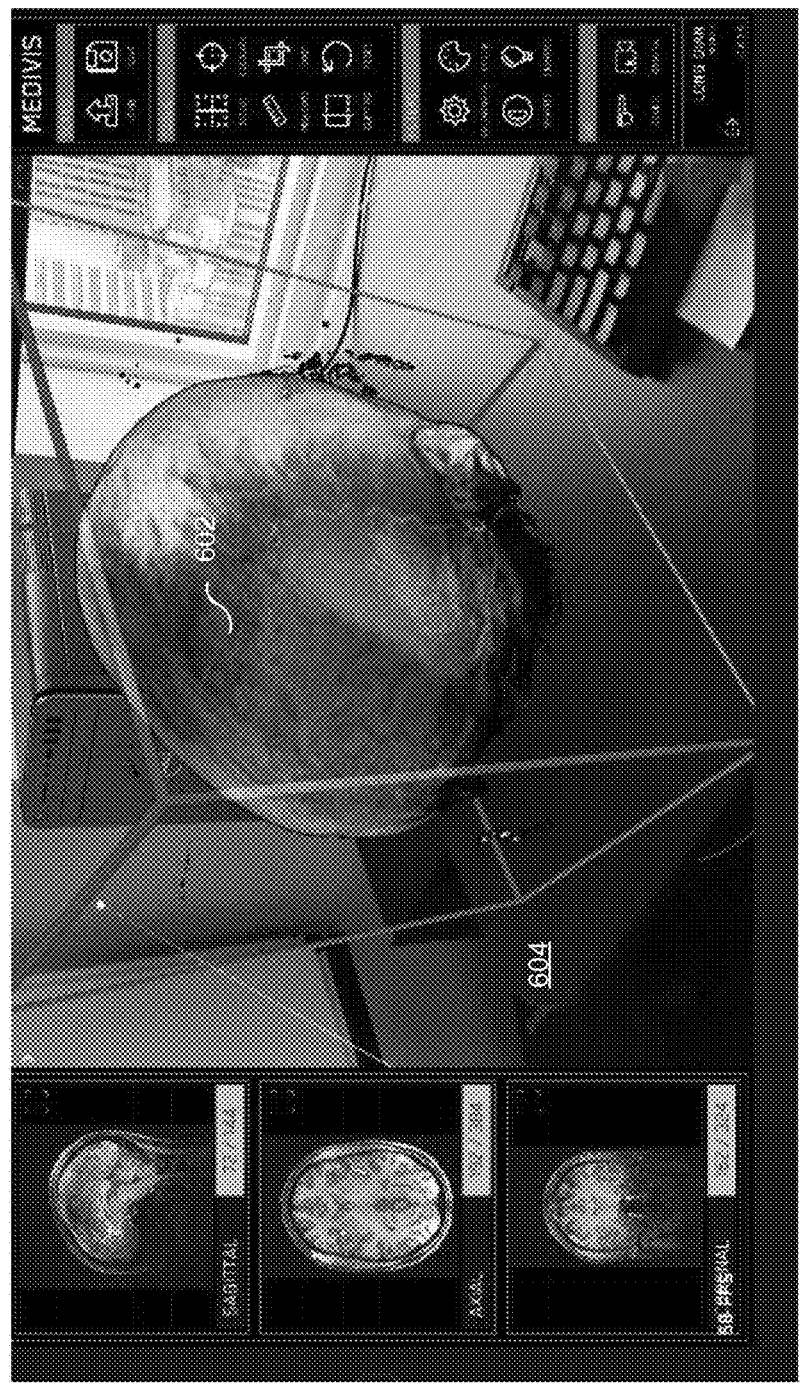
FIGS. 6A and 6B are each a diagram illustrating an exemplary environment in which some embodiments may operate.

As shown FIG. 6A, diagram 600 illustrates a display of a composite image 604 at a workstation during the camera mode. The composite image 604 incorporates a rendering of a 3D model 602 of medical data with display of a view of image data generated by a camera(s) disposed on a smartglass device. As shown in FIG. 6A, the user currently wearing the smartglass device is located at the workstation area and facing substantially directly at the workstation area such that the image data from the camera(s) captures image data for the background of the composite image 604 that portrays the workstation area.

Figure 6B:
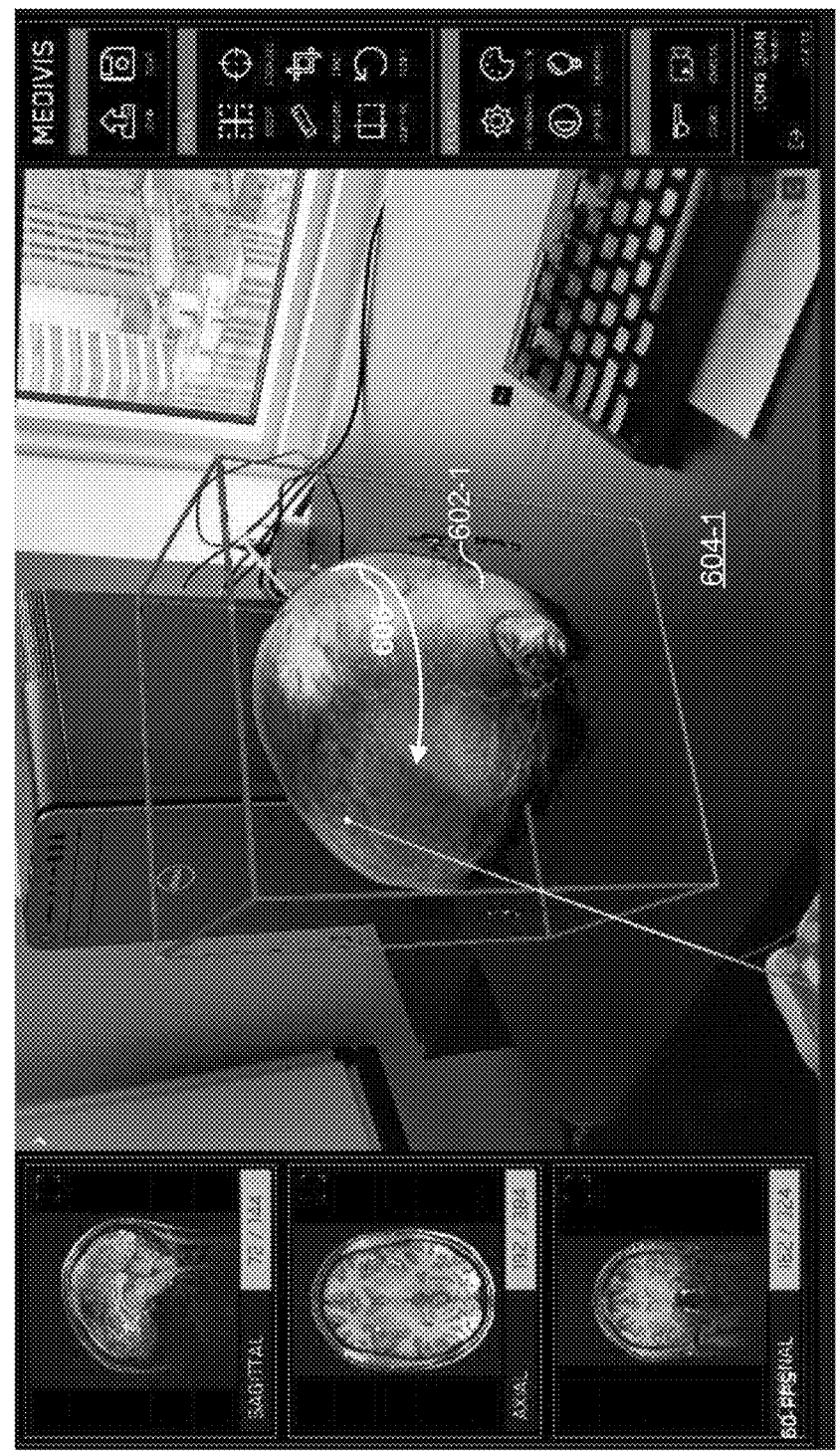

As shown in FIG. 6B, diagram 606 illustrates a display of a composite image 604-1 that reflects physical movement of the user (and/or the user's head) such that the image data of the camera on the smartglass device worn by the user portrays a different view of the workstation area than the view portrayed in FIG. 6A. The rendering 602-1 of the 3D model incorporated into the composite image 604-1 displays a different view of the 3D model based on subsequent camera pose data and/or user manipulation data that occurs after display of the composite image 604 of FIG. 6A.

For example, the user may wear gloves with a sensor(s) associated with the user's smartglass device. The user physically positions a glove within the user's view of the AR image displayed by the smartglass device. The user may trigger a selection of one or more coordinates of the 3D model in the AR image and concurrently perform a gesture, such as a gesture 606 with a direction substantially towards the left. The smartglass device captures user manipulation data that represents the direction and rotation of the gesture 606 in terms of coordinates in the unified coordinate system. The smartglass device sends the user manipulation data for the gesture 606 to the workstation and the workstation generates a base image of the rendering of the 3D model 602-1 based on the user manipulation data. In various embodiments, user manipulation data can be additionally based on a data calculation(s) from real-time sensor data. For example, a depth sensor disposed on a smartglass device may track a user's hand movements and computes respective poses (i.e., rotation, position) of each hand and also computes instances of user interaction events (e.g. clicking, grabbing). It is understood that the smartglass generates base images according to user manipulation data during the distribution mode as well.

Figure 7:
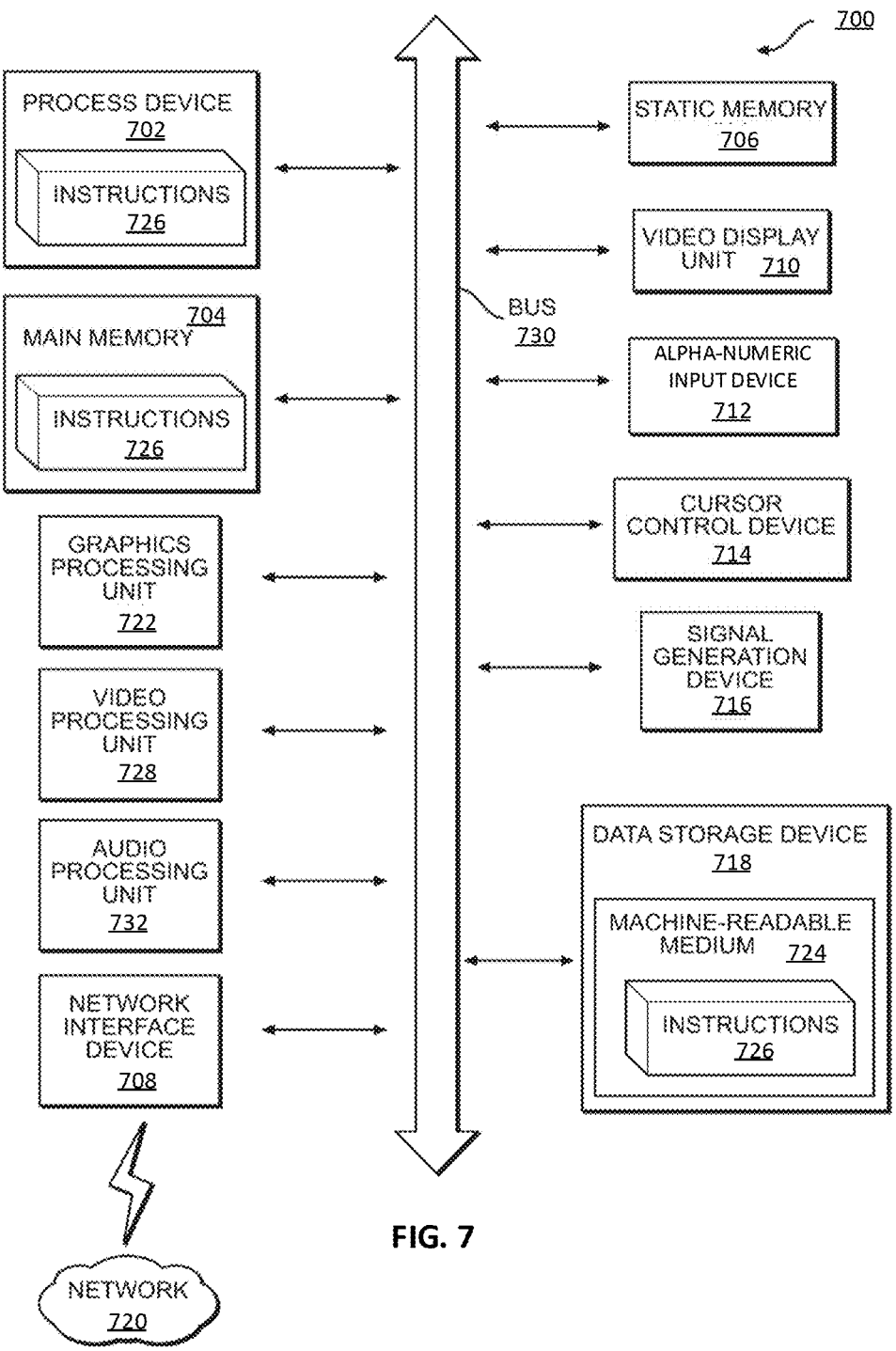
FIG. 7 is a diagram illustrating an exemplary environment in which some embodiments may operate.

FIG. 7 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 700 includes a processing device 702, a main memory 704 (e.g., read-only memory (ROM), flash memory, dynamic random access memory (DRAM) such as synchronous DRAM (SDRAM) or Rambus DRAM (RDRAM), etc.), a static memory 706 (e.g., flash memory, static random access memory (SRAM), etc.), and a data storage device 718, which communicate with each other via a bus 730.

Processing device 702 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 702 may also be one or more special-purpose processing devices such as an application specific integrated circuit (ASIC), a field programmable gate array (FPGA), a digital signal processor (DSP), network processor, or the like. The processing device 702 is configured to execute instructions 726 for performing the operations and steps discussed herein.

The computer system 700 may further include a network interface device 708 to communicate over the network 720. The computer system 700 also may include a video display unit 710 (e.g., a liquid crystal display (LCD) or a cathode ray tube (CRT)), an alphanumeric input device 712 (e.g., a keyboard), a cursor control device 714 (e.g., a mouse), a graphics processing unit 722, a signal generation device 716 (e.g., a speaker), graphics processing unit 722, video processing unit 728, and audio processing unit 732.

The data storage device 718 may include a machine-readable storage medium 724 (also known as a computer-readable medium) on which is stored one or more sets of instructions or software 726 embodying any one or more of the methodologies or functions described herein. The instructions 726 may also reside, completely or at least partially, within the main memory 704 and/or within the processing device 702 during execution thereof by the computer system 700, the main memory 704 and the processing device 702 also constituting machine-readable storage media.

In one implementation, the instructions 726 include instructions to implement functionality corresponding to the components of a device to perform the disclosure herein. While the machine-readable storage medium 724 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method, comprising:
    receiving, at one or more computing systems ("workstation"), camera pose data for a camera mode setting, from at least one camera disposed on a first headset device, the camera pose data representing a physical orientation and position of the camera in a three-dimensional (3D) space as defined by a unified coordinate system;
    at the workstation during an active camera mode setting:
        (i) receiving camera image data comprising one or more images portraying a current view of the camera disposed on the first headset device;
        (ii) generating a rendering of a 3D model of medical data ("3D model") displaying one or more 3D model portions with respective coordinate positions in the unified coordinate system that align with the camera pose data;
        (iii) generating a composite image to include simultaneous and contiguous portrayal of the rendered 3D model with at least a portion of the current view of the camera;
    at the first headset device according to an active distribution mode setting:
        (i) receiving a first base image of the 3D model generated by the workstation, the first base image comprising a transformation of one or more 3D model portions according to first device pose data and first user manipulation data of the first headset device;
        (ii) updating, via post-processing, the first base image, the post-processing accounting for one or more differences in device physical orientation during a latency between a first timestamp of the first base image and a timestamp for an expected time of an upcoming augmented reality (AR) image display based on the first base image.

2. The computer-implemented method of claim 1, further comprising:
    wherein respective device pose data represents a physical orientation and position of a respective headset device according to the unified coordinate system, the device pose data representing a current position and a current rotation of the respective headset device in the 3D space as defined by the unified coordinate system.

3. The computer-implemented method of claim 2, further comprising:
    wherein respective user manipulation data represents at least one change of a position of one or more sensors worn by a user wearing the respective headset device, the sensors associated with the respective headset device, wherein the change of the position of the one or more sensors represents a position change of user-selected portion of an AR image currently displayed as a result of post-processing by the respective headset device, the position change represented by at least one of a direction, rotation and acceleration of the one or more sensors in the 3D space as defined by the unified coordinate system.

4. The computer-implemented method of claim 3, further comprising:
    at the workstation during the active distribution mode setting:
        continually receiving respective device data and respective user manipulation data captured by a plurality of headset devices; and
        concurrently and continually generating and distributing of a plurality of different base images, each different base image generated for distribution for a particular headset device.

5. The computer-implemented method of claim 1, wherein updating, via post-processing, the first base image comprises:
    capturing, at the first headset device, the first predicted device pose data, wherein the first predicted device pose data represents at least one modification of a position and a rotation of the represented in the first device pose data used by the workstation to generate the first base image.

6. The computer-implemented method of claim 1, further comprising:
    at the workstation during the active camera mode setting:
        displaying composite image to include simultaneous and contiguous portrayal of the rendered 3D model with at least a portion of the current view of the camera, wherein the active camera mode setting occurs when the distribution mode setting is inactive.

7. The computer-implemented method of claim 1, further comprising:
    at the first headset device according to the active distribution mode setting:
        generating an AR image based on the updated first base image; and
        displaying the AR image, wherein the active distribution mode setting occurs when the camera mode setting is inactive.

8. A system comprising one or more processors, and a non-transitory computer-readable medium including one or more sequences of instructions that, when executed by the one or more processors, cause the system to perform operations comprising:
    receiving, at one or more computing systems ("workstation"), camera pose data for a camera mode setting, from at least one camera disposed on a first headset device, the camera pose data representing a physical orientation and position of the camera in a three-dimensional (3D) space as defined by a unified coordinate system;
    at the workstation during an active camera mode setting:
        (i) receiving camera image data comprising one or more images portraying a current view of the camera disposed on the first headset device;
        (ii) generating a rendering of a 3D model of medical data ("3D model") displaying one or more 3D model portions with respective coordinate positions in the unified coordinate system that align with the camera pose data;
        (iii) generating a composite image to include simultaneous and contiguous portrayal of the rendered 3D model with at least a portion of the current view of the camera;
    at the first headset device according to an active distribution mode setting:
        (i) receiving a first base image of the 3D model generated by the workstation, the first base image comprising a transformation of one or more 3D model portions according to first device pose data and first user manipulation data of the first headset device;

(ii) updating, via post-processing, the first base image, the post-processing accounting for one or more differences in device physical orientation during a latency between a first timestamp of the first base image and a timestamp for an expected time of an upcoming augmented reality (AR) image display based on the first base image.

9. The system of claim 8, further comprising:
wherein respective device pose data represents a physical orientation and position of a respective headset device according to the unified coordinate system, the device pose data representing a current position and a current rotation of the respective headset device in the 3D space as defined by the unified coordinate system.

10. The system of claim 9, further comprising:
wherein respective user manipulation data represents at least one change of a position of one or more sensors worn by a user wearing the respective headset device, the sensors associated with the respective headset device, wherein the change of the position of the one or more sensors represents a position change of user-selected portion of an AR image currently displayed as a result of post-processing by the respective headset device, the position change represented by at least one of a direction, rotation and acceleration of the one or more sensors in the 3D space as defined by the unified coordinate system.

11. The system of claim 10, further comprising:
at the workstation during the active distribution mode setting:
continually receiving respective device data and respective user manipulation data captured by a plurality of headset devices; and
concurrently and continually generating and distributing of a plurality of different base images, each different base image generated for distribution for a particular headset device.

12. The system of claim 8, wherein updating, via post-processing, the first base image comprises:
capturing, at the first headset device, the first predicted device pose data, wherein the first predicted device pose data represents at least one modification of a position and a rotation of the represented in the first device pose data used by the workstation to generate the first base image.

13. The system of claim 8, further comprising:
at the workstation during the active camera mode setting:
displaying composite image to include simultaneous and contiguous portrayal of the rendered 3D model with at least a portion of the current view of the camera, wherein the active camera mode setting occurs when the distribution mode setting is inactive.

14. The system of claim 8, further comprising:
at the first headset device according to the active distribution mode setting:
generating an AR image based on the updated first base image; and
displaying the AR image, wherein the active distribution mode setting occurs when the camera mode setting is inactive.

15. A computer program product comprising a non-transitory computer-readable medium having a computer-readable program code embodied therein to be executed by one or more processors, the program code including instructions for:
receiving, at one or more computing systems ("workstation"), camera pose data for a camera mode setting, from at least one camera disposed on a first headset device, the camera pose data representing a physical orientation and position of the camera in a three-dimensional (3D) space as defined by a unified coordinate system;
at the workstation during an active camera mode setting:
(i) receiving camera image data comprising one or more images portraying a current view of the camera disposed on the first headset device;
(ii) generating a rendering of a 3D model of medical data ("3D model") displaying one or more 3D model portions with respective coordinate positions in the unified coordinate system that align with the camera pose data;
(iii) generating a composite image to include simultaneous and contiguous portrayal of the rendered 3D model with at least a portion of the current view of the camera;
at the first headset device according to an active distribution mode setting:
(i) receiving a first base image of the 3D model generated by the workstation, the first base image comprising a transformation of one or more 3D model portions according to first device pose data and first user manipulation data of the first headset device;
(ii) updating, via post-processing, the first base image, the post-processing accounting for one or more differences in device physical orientation during a latency between a first timestamp of the first base image and a timestamp for an expected time of an upcoming augmented reality (AR) image display based on the first base image.

16. The computer program product of claim 15, further comprising:
wherein respective device pose data represents a physical orientation and position of a respective headset device according to the unified coordinate system, the device pose data representing a current position and a current rotation of the respective headset device in the 3D space as defined by the unified coordinate system.

17. The computer program product of claim 16, further comprising:
wherein respective user manipulation data represents at least one change of a position of one or more sensors worn by a user wearing the respective headset device, the sensors associated with the respective headset device, wherein the change of the position of the one or more sensors represents a position change of user-selected portion of an AR image currently displayed as a result of post-processing by the respective headset device, the position change represented by at least one of a direction, rotation and acceleration of the one or more sensors in the 3D space as defined by the unified coordinate system.

18. The computer program product of claim 17, further comprising:
at the workstation during the active distribution mode setting:
continually receiving respective device data and respective user manipulation data captured by a plurality of headset devices; and concurrently and continually generating and distributing of a plurality of different base images, each different base image generated for distribution for a particular headset device.

19. The computer program product of claim 15, wherein updating, via post-processing, the first base image comprises:
   capturing, at the first headset device, the first predicted device pose data, wherein the first predicted device pose data represents at least one modification of a position and a rotation of the represented in the first device pose data used by the workstation to generate the first base image.

20. The computer program product of claim 15, further comprising:
   at the workstation during the active camera mode setting:
      displaying composite image to include simultaneous and contiguous portrayal of the rendered 3D model with at least a portion of the current view of the camera, wherein the active camera mode setting occurs when the distribution mode setting is inactive;
   at the first headset device according to the active distribution mode setting:
      generating an AR image based on the updated first base image; and
   displaying the AR image, wherein the active distribution mode setting occurs when the camera mode setting is inactive.

* * * * *